(12) United States Patent
Morita et al.

(10) Patent No.: US 7,008,525 B2
(45) Date of Patent: Mar. 7, 2006

(54) FAIL JUDGING METHOD AND ANALYZER

(75) Inventors: Yoshimitsu Morita, Kyoto (JP); Yoshimi Oura, Kyoto (JP); Teppei Shinno, Onsen (JP)

(73) Assignees: Arkray, Inc., Kyoto (JP); Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/496,041

(22) PCT Filed: Nov. 18, 2002

(86) PCT No.: PCT/JP02/12034

§ 371 (c)(1),
(2), (4) Date: May 19, 2004

(87) PCT Pub. No.: WO03/044513

PCT Pub. Date: May 30, 2003

(65) Prior Publication Data

US 2005/0067301 A1    Mar. 31, 2005

(30) Foreign Application Priority Data

Nov. 20, 2001    (JP)    ............................. 2001-355323

(51) Int. Cl.
*G01N 27/327*    (2006.01)
(52) U.S. Cl. ............... 205/777.5; 204/401; 204/403.01
(58) Field of Classification Search ................ 204/401, 204/403.01–420; 205/775, 777.5, 778, 786–794.5; 324/425, 435, 522, 523
See application file for complete search history.

(56) References Cited

U.S. PATENT DOCUMENTS

| 5,352,351 | A | | 10/1994 | White et al. ................ 204/406 |
| 5,611,909 | A | * | 3/1997 | Studer ......................... 205/775 |
| 2001/0042683 | A1 | | 11/2001 | Musho et al. ............. 205/777.5 |

FOREIGN PATENT DOCUMENTS

| JP | 64-91051 A | * | 4/1989 |
| JP | 4-357452 | | 12/1992 |
| JP | 6-109688 | | 4/1994 |
| JP | 8-502589 | | 3/1996 |
| JP | 2001-66274 | | 3/2001 |
| JP | 2001-66279 | | 3/2001 |

OTHER PUBLICATIONS

Derwent abstract of Kanzaki Paper Mfg. Co. Ltd. JP 64-091051.*
Derwent abstract of Kanzaki Paper Mfg. Co. Ltd. JP 64-091051, Apr. 10, 1989.*

* cited by examiner

*Primary Examiner*—Alex Noguerola
(74) *Attorney, Agent, or Firm*—Hamre, Schumann, Mueller & Larson P.C.

(57) ABSTRACT

An analyzer (A) includes a current measurer (42) for measuring the current flowing between paired electrodes (22a), (22b) when a sample is introduced to the reagent layer (23) of a sensor (2) and voltage is applied across the electrodes, while also including a processor (3) for analyzing the sample based on the current after a predetermined reference time point. The analyzer (A) further includes a fail determiner (44) which monitors the change of the current before and after the reference time point and determines that the sensor (2) is improper when the current change does not correspond to a predetermined current change.

8 Claims, 6 Drawing Sheets

Proper

Fail (Used)

Fail (Exposure)

Fail (Life Expired)

FAIL JUDGING METHOD AND ANALYZER

This application claims priority under 35 U.S.C. 371 from PCT/JP02/12034, filed on Nov. 18, 2002.

TECHNICAL FIELD

The present invention relates to a fail judging method for checking the properness or improperness of a sensor used for analysis such as measurement of the glucose level or cholesterol level of a blood sample. It also relates to an analyzer for implementing such a fail judging method.

BACKGROUND ART

JP-B-2800981 discloses a technique for measuring the concentration of a particular component in a sample such as blood. The prior art is an electrochemical method utilizing a biosensor incorporating a reagent layer and a pair of electrodes. According to the method, a sample is introduced to the reagent layer of the biosensor, with a voltage applied across the paired electrodes, and then the current between the electrodes is measured. Immediately after the sample is introduced to the reagent layer, the current increases as the electrodes and the reagent layer become wet. Thus, the introduction of the sample to the regent layer can be detected based on the fact that the current has reached a predetermined threshold. The component in the sample undergoes reaction with a component in the reagent layer, and the current will change depending on the degree of the reaction. The degree of the reaction depends on the concentration of the particular component in the sample. Therefore, it is possible to calculate the concentration of the particular component in the sample, based on the detection of the current performed when a certain period of time has passed from the preset reference time point, i.e., the time point when the current reaches the predetermined threshold.

To conduct such an analysis, it is desirable that the biosensor to be used is subjected to properness or improperness checking. This is because the user of the analyzer does not always use a proper biosensor. For example, use may be made of a biosensor which was once used, or one which has been unused (exposed) for a long time with its package opened, or one which has undergone the deterioration of the components of the reagent layer because a prolonged period of time has lapsed since the sensor was produced. When the analysis is carried out without finding the user's erroneous use of such an improper biosensor, accurate analysis results cannot be obtained and the analysis itself is useless. Further, the user may mistake such inaccurate analysis results for accurate ones.

No means of performing accurate checking for improper sensors has been proposed so far. The above-mentioned JP-B-2800981 teaches means for detecting an insufficient supply of a sample to the reagent layer. However, it is difficult to accurately detect the improperness of the biosensor by such means.

DISCLOSURE OF THE INVENTION

An object of the present invention is to provide a fail judging method capable of solving the above-described problems. Another object of the present invention is to provide an analyzer capable of properly performing such a fail judging method.

According to a first aspect of the present invention, there is provided a fail judging method for determining the properness or improperness of a sensor used for analysis of a sample. The analysis comprises: introducing the sample to a reagent layer of the sensor; applying a voltage to the reagent layer and the sample via a pair of electrodes; measuring the current between the electrodes; setting a reference time point as a time point when the current reaches a predetermined threshold for detection of the introduction of the sample; and obtaining an analysis result based on the current measured after the reference time point. The method comprises: observing change of the current before and after the reference time point; and determining that the sensor is improper when the change of the current differs from a predetermined change.

With such a fail judging method, whether or not the sensor is proper can be judged accurately. Specifically, the manner of the current change over a certain period around the reference time point is different depending on whether the sensor is proper or improper. In the present invention, whether the sensor is proper or not can be determined based on the difference of the manner of the current change. Particularly, in the present invention, the manner of the current change before the reference time point is also taken into consideration in addition to that after the reference time point, whereby more accurate fail judgment can be performed. According to the present invention, therefore, it is possible to eliminate or lessen the possibility that ineffective analysis is performed by overlooking the use of an improper sensor or that the user believes the inaccurate results obtained by such ineffective analysis to be accurate.

Preferably, in the present invention, it is determined that the sensor is proper, if the current flowing between the paired electrodes increases monotonously in a wider sense for a prescribed period of time after the sample is introduced and if the current increases monotonously in a strict sense with its gradient falling in a predetermined range for a prescribed period of time after the reference time point. Otherwise, it is determined that the sensor is improper.

In this specification, "monotonous increase in a wider sense" means a monotonous increase in a sequence an that satisfies the relation $a_1\ a_2\ a_3\ \ldots$, thereby including the case where the increment is zero. The "monotonous increase in a strict sense" means a monotonous increase in a sequence $a_n$ that satisfies the relation $a_1 < a_2 < a_3 < \ldots$, thereby excluding the case where the increment is zero.

According to a second aspect of the present invention, there is provided an analyzer comprising: a sensor mount portion for mounting a sensor which includes a reagent layer to which a sample is introduced and a pair of electrodes for applying voltage to the reagent layer; a current measurer for measuring current between the electrodes when voltage is applied across the electrodes; and a processor for analyzing the sample based on current after a reference time point which is preset for a time point when the current measured by the current measurer reaches a predetermined threshold for detection of the introduction of the sample. The analyzer comprises a fail determiner for monitoring change of the current before and after the reference time point and for determining that the sensor is improper when the change of the current differs from a predetermined change.

With such an analyzer, it is possible to properly implement the fail judging method provided by the first aspect of the present invention, whereby advantages as described above can be enjoyed.

Preferably, the reagent layer causes the current flowing between the electrodes to exhibit a monotonous increase in a wider sense for a certain period after the sample is introduced, while the fail determiner determines that the sensor is proper when the current changes to exhibit only a monotonous increase in a strict sense with a gradient in a predetermined range for a predetermined period after the reference time point. Otherwise, the sensor is determined to be improper.

Preferably, the present invention further comprises a notifier for providing a notice when the fail determiner determines that the sensor is improper.

Preferably, the reagent layer contains an electron acceptor. Further, the fail determiner determines that the sensor is a used one and the notifier notifies this determination when the current changes from an increase to a decrease during a predetermined period around the reference time point and exhibits a peak value larger than a predetermined value.

In this specification, the "electron acceptor" refers to a substance that receives electrons from a particular component of a sample when the sample is introduced, and releases the electrons when a voltage is applied.

Preferably, the fail determiner determines that the sensor has been exposed over a certain period and the notifier notifies this determination when the current changes from an increase to a decrease during a predetermined period around the reference time point and exhibits a peak value no larger than a predetermined value.

Preferably, the fail determiner determines that life of the sensor has expired and the notifier notifies this determination when the sensor is determined to be improper and the current does not change from an increase to a decrease during a predetermined period around the reference time point.

Other features and advantages of the present invention will become clearer from the description of the embodiments of the invention given below.

BRIEF DESCRIPTION OF THE DRAWINGS

FIG. 5A is a time chart of voltage applied across the electrodes of the biosensor, whereas

BEST MODE FOR CARRYING OUT THE INVENTION

Preferred embodiments of the present invention will be described below with reference to the accompanying drawings.

Figure 1:
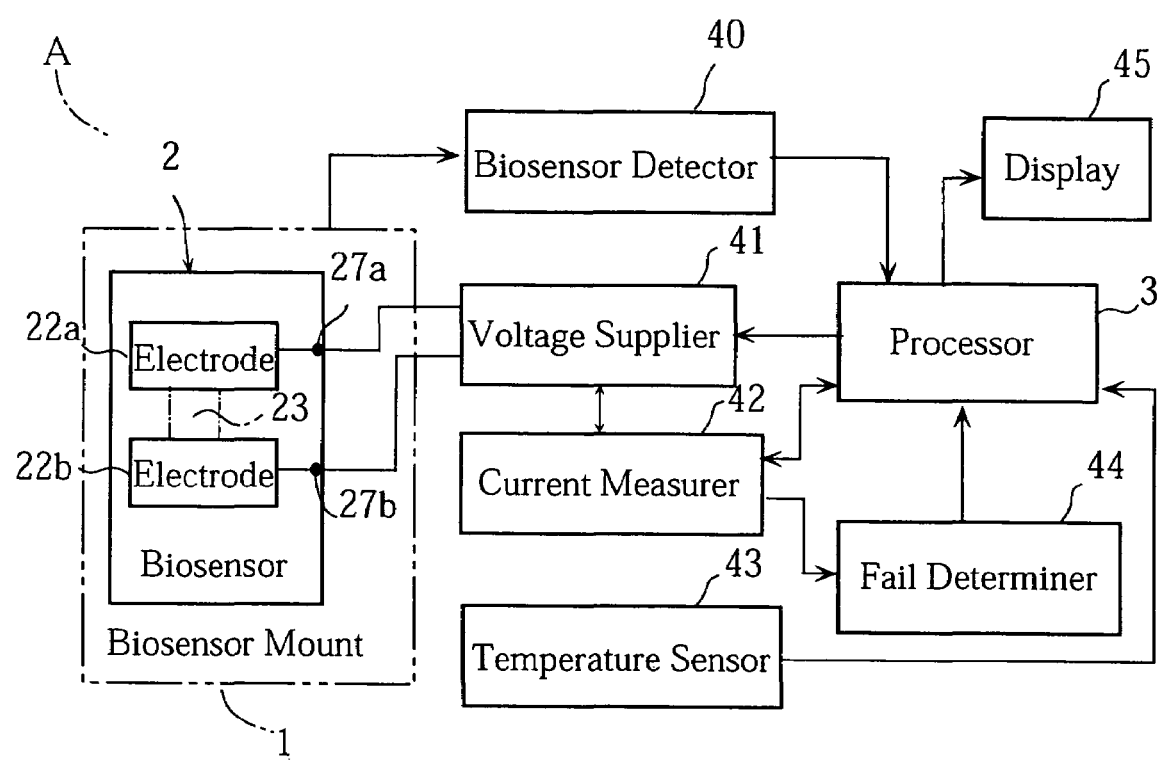
FIG. 1 is a circuit block diagram showing an example of analyzer according to the present invention.

FIG. 1 shows an example of analyzer according to the present invention. The analyzer A of the illustrated embodiment utilizes a biosensor 2 shown in FIGS. 2 and 3.

Figure 2:
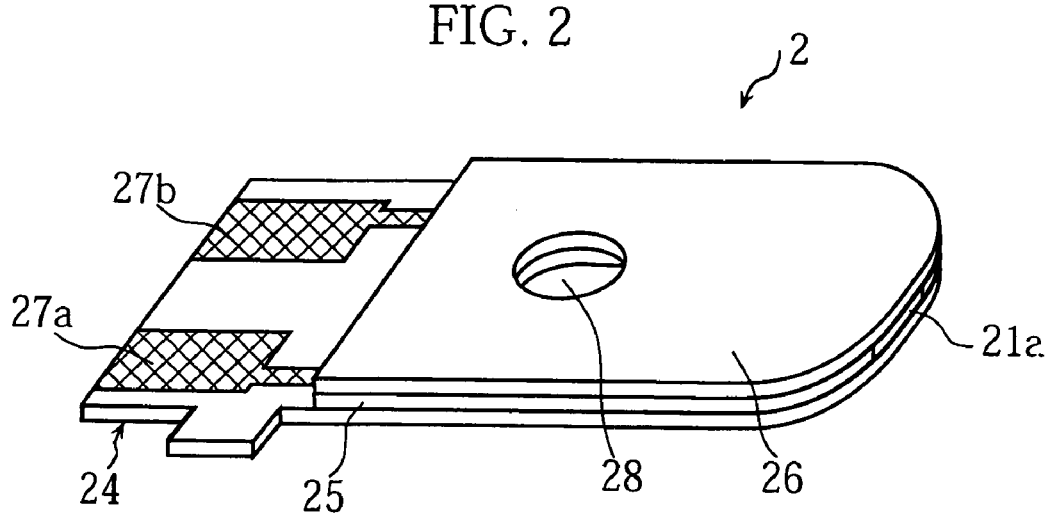
FIG. 2 is a perspective view illustrating an example of biosensor.
Figure 3:
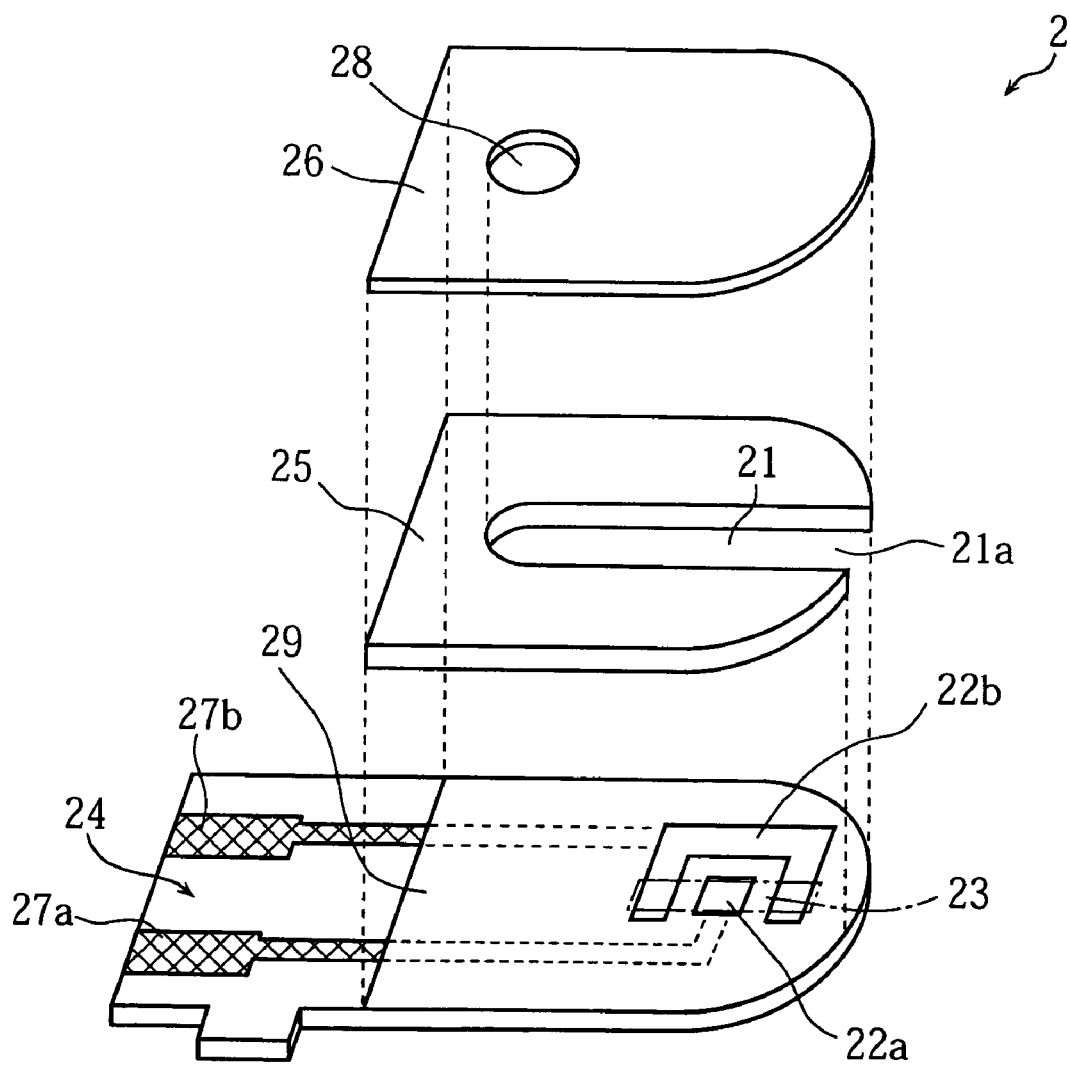
FIG. 3 is an exploded perspective view of the biosensor shown in FIG. 2.

As shown in FIGS. 2 and 3, the biosensor 2 includes a substrate 24 having an upper surface on which a pair of electrodes 22a and 22b, and a reagent layer 23 are provided.

The reagent layer 23 bridges between the paired electrodes 22a and 22b. The reagent layer 23 contains glucose oxidase (hereinafter abbreviated as "GOD") and potassium ferricyanide as components to react with glucose in blood, for example. Potassium ferricyanide is an example of electron acceptor. The meaning of the electron acceptor is described above. Portions around the reagent layer 23 and the electrodes 22a, 22b are covered with an insulating film 29. Aside of the insulating film 29 is provided terminals 27a and 27b electrically connected to the electrodes 22a and 22b.

On the substrate 24, a spacer 25 and a cover 26 are laminated. The spacer 25 is formed with a narrow slit 21. When a liquid sample is applied to the front end opening 21a of the slit 21, the sample proceeds through the slit 21 by capillary action to be introduced to the reagent layer 23.

In order to realize the capillary action properly, the cover 26 is formed with a hole 28 which allows part of the slit 21 to communicate with the outside.

As shown in FIG. 1, the analyzer A in this embodiment includes a biosensor mount portion 1, a processor 3, a biosensor detection circuit 40, a voltage supply circuit 41, a current measuring circuit 42, a temperature sensor 43, a fail determiner 44 and a display 45.

The biosensor mount portion 1 has a structure that allows the removable attachment of the biosensor 2. When the biosensor 2 is mounted to the biosensor mount portion 1, the terminals 27a and 27b of the biosensor 2 are electrically connected to the voltage supply circuit 41. The processor 3, which may comprise a CPU and an appropriate memory connected thereto, performs operation control at each of the units and data processing, which will be described later. The voltage supply circuit 41 applies a predetermined voltage across the paired electrodes 22a and 22b of the biosensor 2 under the control of the processor 3. The current measuring circuit 42 measures the current between the electrodes 22a and 22b and outputs the measurement data to the processor 3 and the fail determiner 44. The current measurement is performed in a predetermined cycle (e.g. in a cycle of 50 ms).

The fail determiner 44 functions to determine whether or not the biosensor 2 is proper based on the change of the current measured by the current measuring circuit 42. The method of fail determination will be described later in detail. The fail determiner 44 may be provided as an integral part of the processor 3. The biosensor detection circuit 40 detects the biosensor 2 when the biosensor is properly mounted to the biosensor mount portion 1 and outputs a signal to that effect to the processor 3. The temperature sensor 43 measures the ambient temperature of the biosensor 2 and outputs the measurement data to the processor 3. The display 45 displays a required image under the control of the processor 3 and may comprise a liquid crystal display or a CRT, for example. The display 45 is an example of notifier in the present invention.

Next, referring to the flowchart shown in FIG. 4, description will be made of the analysis process using the biosensor 2 and the analyzer A, the manner of fail determination in the process, and the operation of the processor 3. In this embodiment, the measurement of the glucose level in sampled blood will be exemplarily described.

Figure 5A:
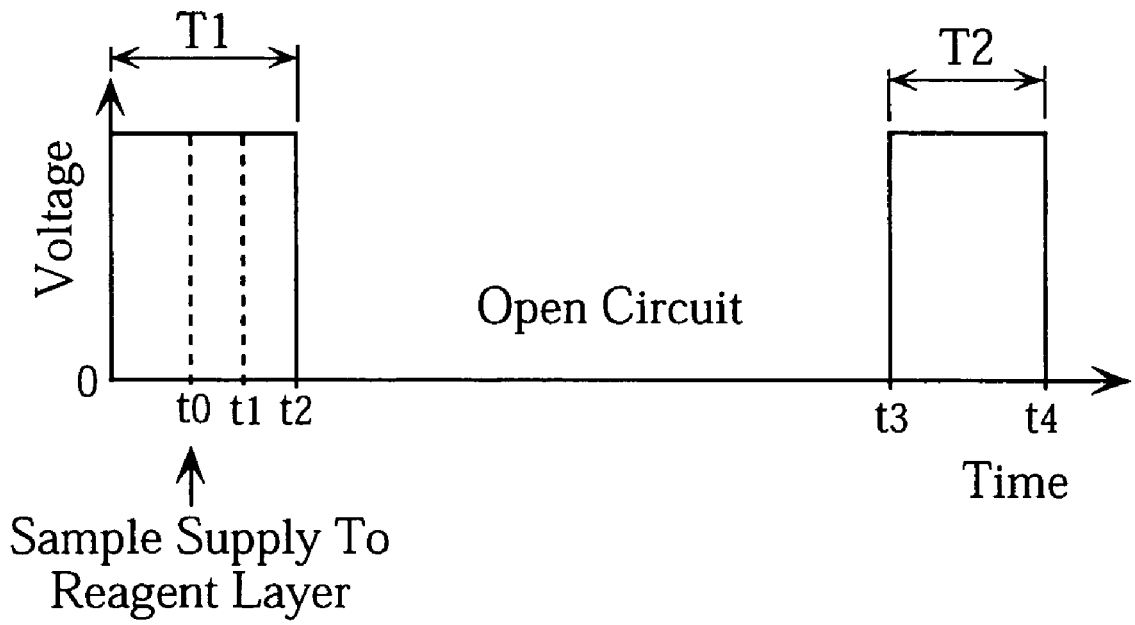

First, when the biosensor 2 is mounted to the biosensor mount portion 1 and the mounting is detected by the biosensor detection circuit 40 (S1: YES), the processor 3 stores the data on the temperature detected by the temperature sensor 43 (S2). The temperature data can be later utilized for correcting the measurement value of the glucose level. Subsequently, the processor 3 drives the voltage supply circuit 41 to apply a voltage of e.g. about 500 mV across the electrodes 22a and 22b of the biosensor 2 (S3). Then, the current measuring circuit 42 starts to measure the current between the electrodes 22a and 22b (S4). Specifically, as shown in FIG. 5A, voltage is applied across the electrodes 22a and 22b twice, i.e. for a period T1 and for a period T2. As will be described later, the first voltage application for the period T1 is performed for the fail determination in the analysis process, whereas the second voltage application for the period T2 is performed for the glucose level measurement.

Figure 5B:
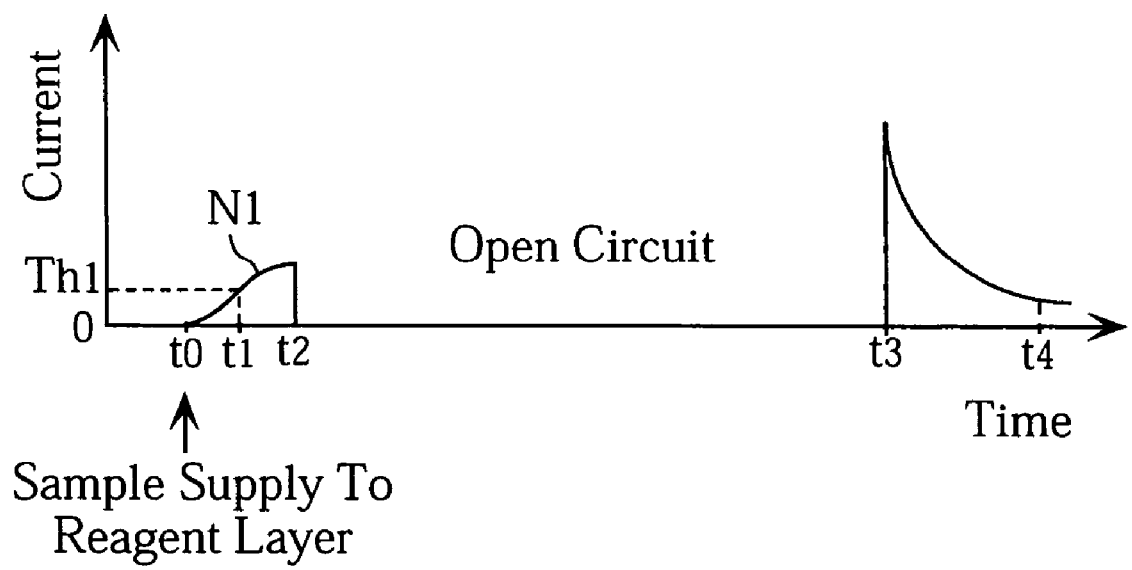
FIG. 5B is a time chart of current flowing between the electrodes of the biosensor.

When blood is introduced to the reagent layer 23 of the biosensor 2 during the period T1 of the first voltage application, electrical conduction is established between the electrodes 22a and 22b. Therefore, as indicated by the curved line N1 in FIG. 5B, the current between the electrodes 22a and 22b continues to increase after the time point t0 at which the blood is introduced. When the current reaches a predetermined threshold Th1, the processor 3 determines that the blood has been introduced to the reagent layer 23 (S5: YES). This time point t1 is set as a reference time point.

When predetermined time (e.g. one second) has elapsed since the time t1 (S6: YES), the processor 3 stops the first voltage application and causes the fail determiner 44 to perform the fail determination (S7). The description of the fail determination will be given later, since the glucose level measurement should be understood for the understanding of the fail determination. When the biosensor 2 is found to be proper as a result of the fail determination (S8: YES), the processor 3 performs control for the glucose level measurement (S9) and causes the display 45 to display the result (S10).

As shown in FIG. 5A, in the measurement of the glucose level, the voltage application across the electrodes 22a and 22b is suspended for a predetermined period of time (e.g. 25 seconds) after time t2 at which the first voltage application is stopped, for the purpose of promoting the reaction of glucose in blood with GOD and potassium ferricyanide in the reagent layer 23. After the predetermined period has elapsed, that is, at time t3, the second voltage application to the electrodes 22a and 22b is begun. The applied voltage may be 500 mV, for example. Then, at time t4, which is after a predetermined period (e.g. five seconds) has elapsed since the time t3, the current between the electrodes 22a and 22b is measured and the glucose level is figured out based on the measurements. The reactions in these processes are represented by the following formulas:

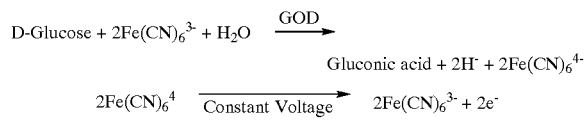

The current flowing during the second voltage application is proportional to the concentration of potassium ferrocyanide generated by the above reaction. The concentration of potassium ferrocyanide is proportional to the glucose level in blood. Therefore, the glucose level can be figured out based on the current detected at the time t4.

Now, the fail determination will be described in detail.

A biosensor 2 is either proper or improper, and as discussed below, this alternative gives rise to the difference in the current behavior observed before and after the time t1.

Figure 6A:
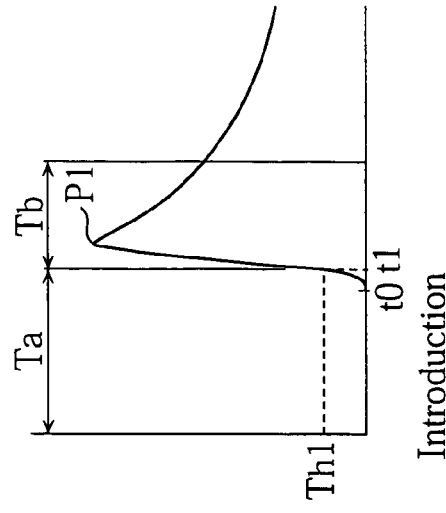
FIGS. 6A–6D show examples of the change of the current flowing between the electrodes of the biosensor.

When the biosensor 2 is proper, the current passing between the paired electrodes 22a, 22b will increase monotonously only in the wider sense, as shown in FIG. 6A, for about one second immediately after the time t0 at which the blood is introduced. More precisely, the current increases monotonously only in the wider sense during the period Ta before the reference time t1, and it increases monotonously only in the strict sense during the period Tb (about a fraction of a second) after the time t1, with finite gradients in a certain range. In this case, the increase of current traces a relatively smooth curve or generally straight line, whereby the gradient does not change abruptly. This is because the reagent layer 23 of the biosensor 2 and the particular component of the sample have reacted only slightly immediately after the sample is introduced, and thereafter the response current gradually increases as the reaction proceeds.

Figure 6B:
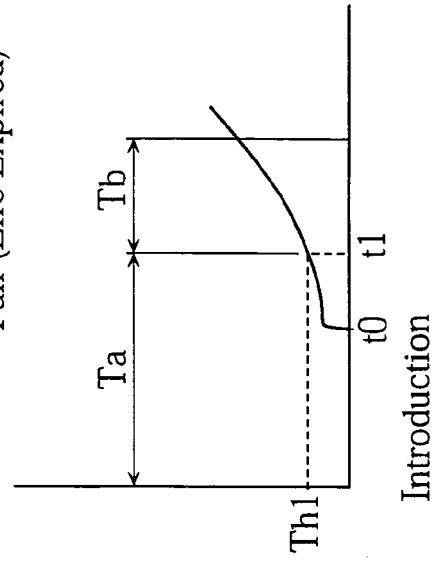

In a situation different from the above case, the biosensor 2 may have been used before and left in a dried state. In this case, as shown in FIG. 6B, the current increases steeply after the introduction of blood to the reagent layer 23 and then decreases. Specifically, in the period Ta before the time t1, the current exhibits a monotonous increase only in the wider sense, as in the case of FIG. 6A. However, in the period Tb after the time t1, the current exhibits a peculiar behavior, i.e., a sudden change from the monotonous increase in the wider sense to an decrease. This may be because, in the case where the biosensor 2 was already used for the glucose level measurement, potassium ferrocyanide carrying electrons remains in the reagent layer 23, and the electrons are released from the potassium ferrocyanide all at once in a certain period immediately after the blood introduction.

Figure 6C:
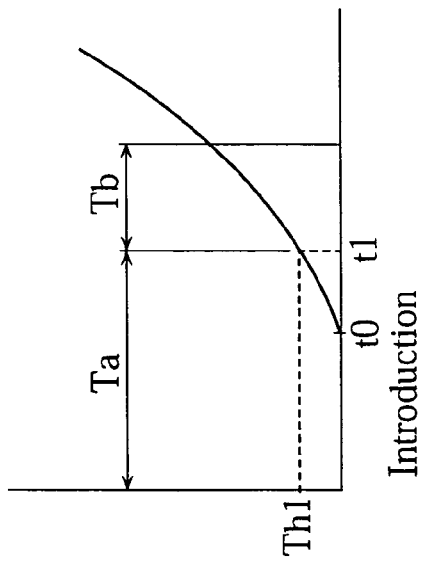

When the biosensor 2 has been exposed to the air for a long period and hence the reagent layer 23 has absorbed moisture from the air over a predetermined amount, the current increases steeply immediately after the blood introduction to the reagent layer 23, as shown in FIG. 6C. Thereafter, however, the current decreases for a certain period and then changes to a monotonous increase in the wider sense, as shown in the figure. Specifically, similarly to the case shown in FIG. 6B, the current changes from an increase to a decrease in the periods Ta, Tb before and after the time t1. Although such a change occurs before the time t1 in the graph of FIG. 6C, it occurs after the time t1 if a smaller value is set as the threshold Th1. Conceivably, this change may occur because, when the reagent layer 23 contains much moisture, the conductivity is enhanced immediately after the blood is introduced. In the case of FIG. 6C, the peak value P2 at which the current changes from an increase to a decrease is considerably smaller than the peak value P1 in the case of FIG. 6B.

Figure 6D:
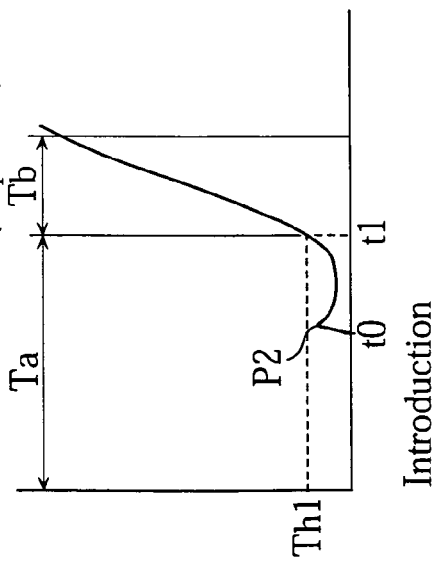

FIG. 6D shows a case where the life of the biosensor 2 has expired after the sensor has been left for a certain period of time, with its package sealed. The current increases sharply immediately after the blood introduction to the reagent layer 23 and then increases gently. In this case, unlike the case shown in FIG. 6C, the up-and-down phenomenon of the current does not occur. The change of the current in this case occurs due to the change of the composition of the reagent layer 23 with time. The gradient after the time t1 is smaller than when the biosensor 2 is proper.

Figure 7:
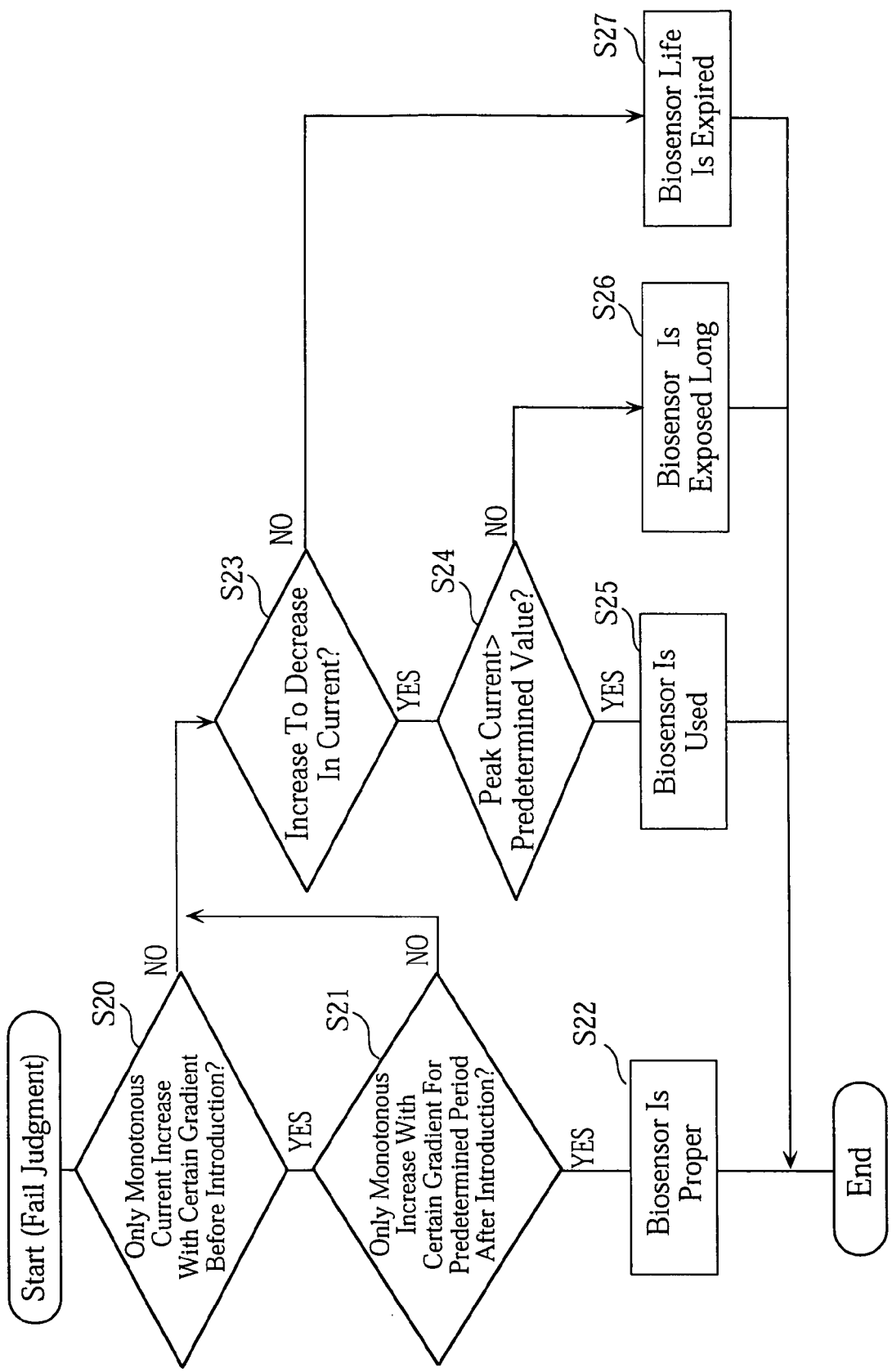
FIG. 7 is a flowchart showing the process of the fail judging.

The data on the current behaviors described above is stored in the fail determiner 44 in advance. The fail determiner 44 determines which of these behaviors represents the actual current change measured by the current measuring circuit 42. This operation is illustrated in the flowchart of FIG. 7.

If the current exhibits a monotonous increase in the wider sense with a gradient in a predetermined range before the time t1 at which the sample introduction is detected (S20: YES) and if the current exhibits only a monotonous increase in the strict sense with a gradient in a predetermined range in the period Tb after the detection of the sample introduction (S21: YES), it is determined that the biosensor 2 is proper (S22).

On the other hand, when the current does not exhibit the above-described changes (S20: NO, S21: NO) and does not change from an increase to a decrease in the periods Ta, Tb (S23: NO), it is determined that the life of the biosensor 2 has expired (S27). As described above with reference to FIG. 6D, the current will exhibit only a monotonous increase in the wider sense when the life of the biosensor 2 has expired. In this case, however, the current will increase sharply immediately after the blood introduction, whereby the gradient may become greater than a prescribed value. Thereafter, the rate of the current increase may abruptly become smaller so that the gradient may become smaller than a prescribed value. In light of this, it is possible to properly determine weather the biosensor 2 has expired or not, by checking weather the gradient of the current increase lies in a predetermined range or not.

Differing from the above case, when the current changes from an increase to a decrease during the period Ta, Tb (S23: YES) and the peak value is larger than a predetermined value (S24: YES), it is determined that the biosensor 2 is a used one (S25). When the peak value is no larger than the predetermined value (S24: NO), it is determined that the biosensor 2 has been exposed for a long time (S26).

Figure 4:
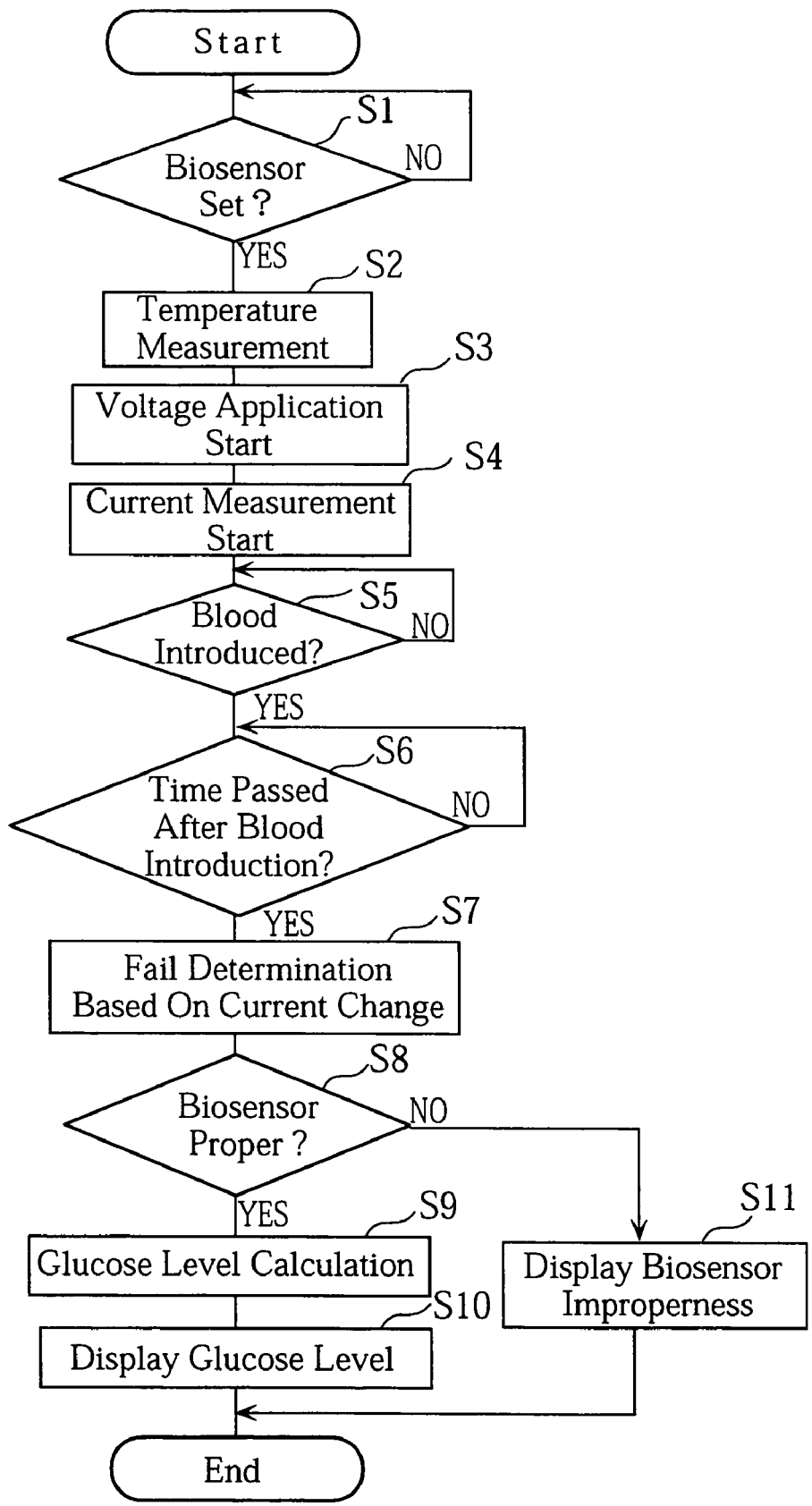
FIG. 4 is a flowchart showing the control operation by the processor of the analyzer shown in FIG. 1.

When the biosensor 2 is determined to be improper in the fail determination (S8 in FIG. 4: NO), the processor 3 causes the display 45 to display the improper state specifically (S11) and interrupts the process. Seeing the display, the user can know the improperness of the biosensor 2 and the reason thereof. As a result, the user can try to perform proper glucose level measurement with the use of a proper biosensor 2. This, however, limits the present invention. Even when the biosensor 2 is found improper, the glucose level measurement may be performed to display the measurement result at the display 45 for reference data.

The present invention is not limited to the above-described embodiment. The specific arrangement of each step of the fail determination method may be modified in various ways. The specific structure of each part of the analyzer according to the present invention may also be modified in various ways.

For instance, in the foregoing embodiment, a used biosensor, a biosensor exposed to the air and a biosensor whose life has expired are described as examples of improper biosensor. However, when change of the current which does not correspond to any of these cases is observed, the display may show that the biosensor is improper because of any other reason. Moreover, in the present invention, the specific reason of the impropriety of the sensor need not necessarily be informed, and determination may be made only as to whether or not the biosensor is proper.

In this embodiment, the fail determination is made based on the change of current during a predetermined period around a predetermined reference time. The length of the period is determined appropriately based on the conditions such as the reagent layer, the sample and the applied voltage. Moreover, the threshold for detecting the sample introduction is not limited to a specific value. Although a shorter current measurement cycle enables more accurate fail determination, the cycle is not limitative.

In measuring the current, the measurements may include noise. It is preferable that the fail determination of the present invention is performed based on the change of the current value after such noise is eliminated.

In the present invention, the kind of the sample or the reagent layer is not limited to a specific one. Further, use may be made of a sensor which is different in structure from that of the foregoing embodiment. As the notifier, use may be made of means which draws the user's attention by turning on a lamp or by sounding an alarm.

The invention claimed is:

1. A fail judging method for determining properness or improperness of a sensor used for analysis of a sample, the analysis comprising:
   introducing the sample to a reagent layer of the sensor;
   applying a voltage to the reagent layer and the sample via a pair of electrodes;
   measuring current between the electrodes;
   setting a reference time point as a time point when the current reaches a predetermined threshold for detection of the introduction of the sample; and
   obtaining an analysis result based on current measured after the reference time point;
   wherein the method comprises:
   observing change of the current before and after the reference time point; and
   determining that the sensor is improper when the change in current before the reference time point or the change in current after the reference time point differs from a predetermined change before the reference time point or a predetermined change after the reference time point, respectively.

2. The fail judging method according to claim 1, wherein the reagent layer causes current flowing between the electrodes to exhibit a monotonous increase in a wider sense for a certain period after the sample is introduced, and
   wherein the sensor is determined to be proper when the current changes to exhibit only a monotonous increase in a strict sense with a gradient falling in a predetermined range for a predetermined period after the reference time point, whereas otherwise the sensor is determined to be improper.

3. The fail judging method according to claim 1,
   wherein the sensor is determined to be a used one when the current changes from an increase to a decrease during a predetermined period around the reference time point and exhibits a peak value larger than a predetermined value.

4. The fail judging method according to claim 1, wherein the sensor is determined to have been exposed over a certain period when the current changes from an increase to a decrease during a predetermined period around the reference time point and exhibits a peak value no larger than a predetermined value.

5. The fail judging method according to claim 1, wherein life of the sensor is determined to have expired when the sensor is determined to be improper and the current does not change from an increase to a decrease during a predetermined period around the reference time point.

6. An analyzer comprising:
   a sensor mount portion for mounting a sensor which includes a reagent layer to which a sample is introduced and a pair of electrodes for applying voltage to the reagent layer;
   a current measurer for measuring current between the electrodes when voltage is applied across the electrodes; and
   a processor adapted for analyzing the sample based on current after a reference time point which is preset for a time point when the current measured by the current measurer reaches a predetermined threshold for detection of the introduction of the sample;

wherein the analyzer comprises a fail determiner adapted for monitoring change of the current before and after the reference time point and for determining that the sensor is improper when the change in current before the reference time point or the change in current after the reference time point differs from a predetermined change before the reference time point or a predetermined change after the reference time point, respectively.

7. The analyzer according to claim 6, wherein the reagent layer causes current flowing between the electrodes to exhibit a monotonous increase in a wider sense for a certain period after the sample is introduced, and wherein the fail determiner determines that the sensor is proper when the current changes to exhibit only a monotonous increase in a strict sense with a gradient in a predetermined range for a predetermined period after the reference time point, whereas otherwise the determiner determines that the sensor is improper.

8. The analyzer according to claim 6, further comprising a notifier for providing a notice when the fail determiner determines that the sensor is improper.

* * * * *